United States Patent [19]

Abbott et al.

[11] Patent Number: 4,565,448
[45] Date of Patent: Jan. 21, 1986

[54] PARTICLE COUNTING APPARATUS

[75] Inventors: Scot D. Abbott; Charles W. Robertson, Jr, both of Wilmington, Del.

[73] Assignee: E. I. Du Pont de Nemours and Company, Wilmington, Del.

[21] Appl. No.: 474,482

[22] Filed: Mar. 11, 1983

[51] Int. Cl.$^4$ ............................................. G01N 15/02
[52] U.S. Cl. .................................... 356/336; 356/339; 356/246
[58] Field of Search ............... 356/336, 338, 339, 246; 250/564, 574, 576, 222.2, 461.2; 377/10, 11

[56] References Cited

U.S. PATENT DOCUMENTS

| | | | |
|---|---|---|---|
| 2,779,232 | 1/1957 | Small | 377/10 |
| 3,531,211 | 9/1970 | Staunton | 356/244 |
| 3,661,460 | 5/1972 | Elking et al. | 356/36 |
| 3,700,338 | 10/1972 | Trundle | 356/246 |
| 3,701,620 | 10/1972 | Berkman et al. | 356/246 |
| 3,703,641 | 11/1972 | Rosen | 250/218 |
| 3,720,470 | 3/1973 | Berkhan | 356/102 |
| 3,788,744 | 1/1974 | Friedman et al. | 356/39 |
| 3,790,760 | 2/1974 | Stiller | 235/92 |
| 3,989,381 | 11/1976 | Fulwyler | 356/39 |
| 4,115,011 | 9/1978 | Brunsting | 356/246 |
| 4,136,953 | 1/1979 | Klein et al. | 356/339 |
| 4,198,161 | 4/1980 | Larson | 356/339 |
| 4,348,107 | 9/1982 | Leif | 356/72 |

OTHER PUBLICATIONS

Brochure entitled "Particle Size Analyser HC-15", by Polytec Optronics, Inc.
Olsen, Modern Optical Methods of Analysis, McGraw Hill (1975), pp. 456–459.

Primary Examiner—Davis L. Willis
Assistant Examiner—Matthew W. Koren

[57] ABSTRACT

A particle counting apparatus includes a cuvette having a cylindrical bore therethrough and an exterior cylindrical surface the axis of which is perpendicular to the axis of the bore. The apparatus is adapted to detect light scattered from a particle that is small as compared to the wavelength of incident radiation and has an index of refraction close to that of the medium in which it is entrained.

20 Claims, 5 Drawing Figures

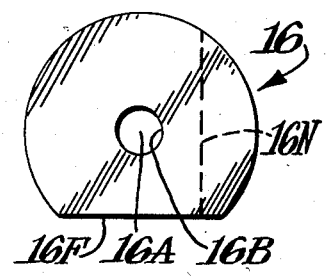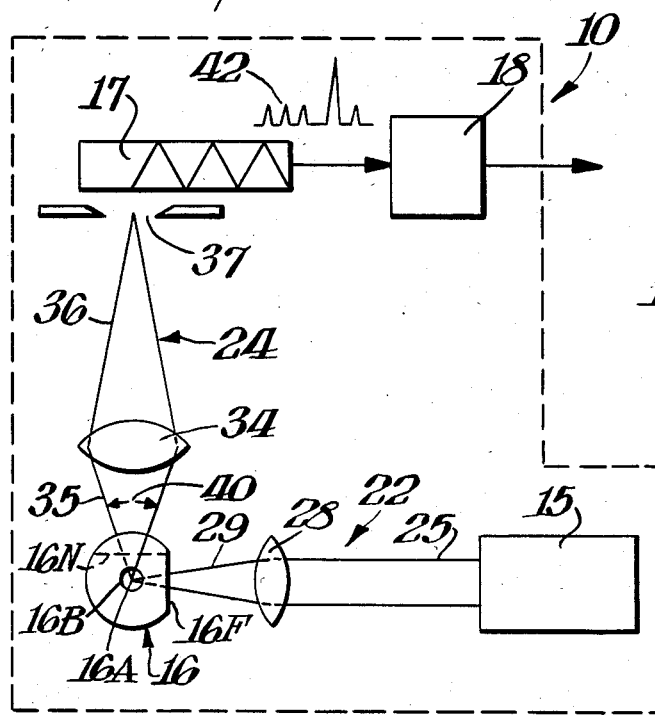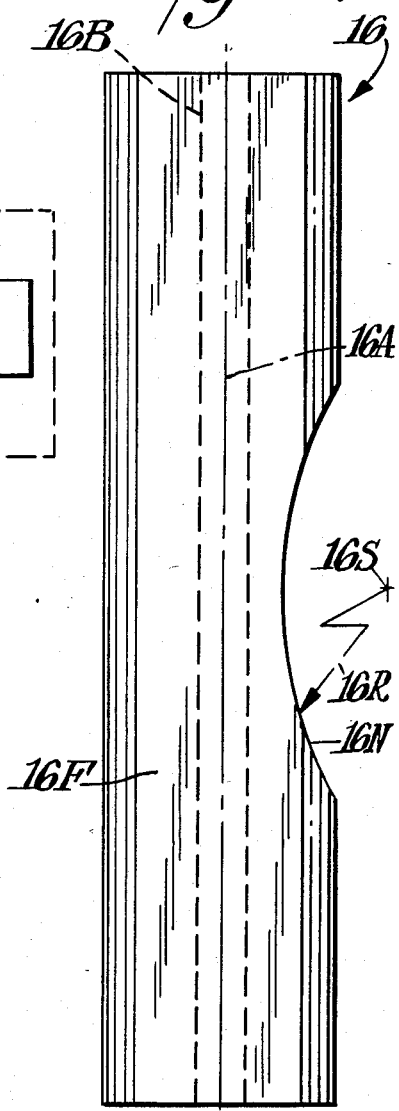

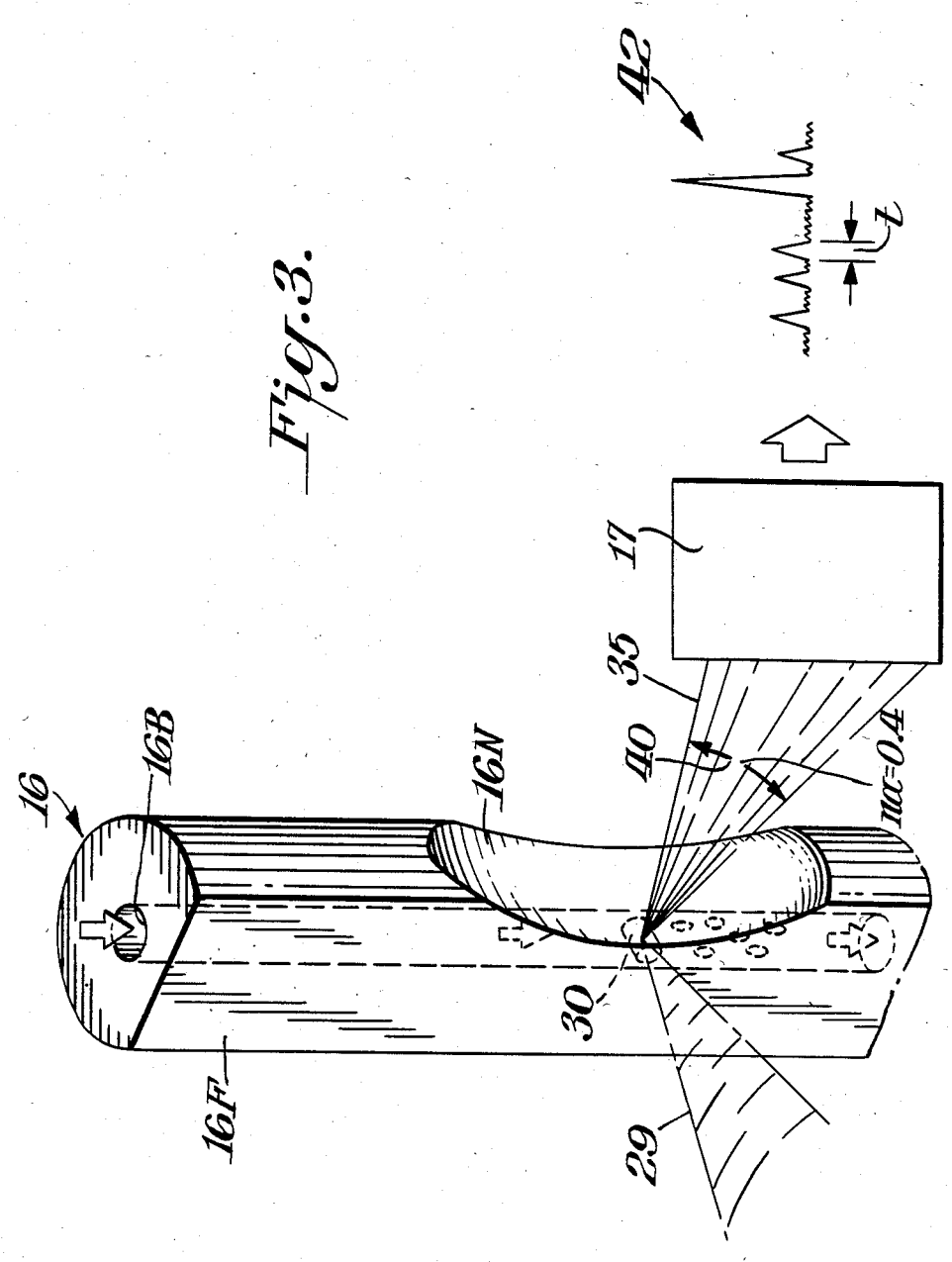

PARTICLE COUNTING APPARATUS

BACKGROUND OF THE INVENTION

This invention relates to an apparatus for counting particles entrained in a fluid medium flow and, in particular, to an apparatus adapted to count and to resolve particles having sizes that are small as compared to the illuminating wavelength and/or have an index of refraction close to that of the medium.

Subject matter disclosed herein is disclosed in the copending application of S. D. Abbott et al. titled "Particle Reagent Size Distribution Measurements for Immunoassay", Ser. No. 474,483, U.S. Pat. No. 4,521,521 and the copending application of S. D. Abbott titled "Particle Counting System For A Fractionating Device," Ser. No. 474,481, both filed contemporaneously herewith.

Particle size analysis and counting instruments based upon light scattering techniques adapted to count particles entrained in aerosol and translucent fluid medium (primarily liquid) flows are known. Exemplary of such apparatus is that sold by Polytec Optronics, Incorporated of El Toro, Calif. as model HC15. It is often of advantage to obtain a histogram by count or other representation of the number of particles having sizes that are small as compared to the illuminating wavelength and/or that have an index of refraction close to the index of refraction of the medium. However, such apparatus as is commercially available is not believed able to provide quantitative measurements of the number of particles having such sizes or indices of refraction.

The Mie Theory relates to the radiation scattering properties of particles that are small as compared to the free space wavelength of the incident radiation. See, generally, Kerker, "The Scattering of Light and Other Electromagnetic Radiation", Academic Press, Inc. (1969). For purposes of this application, the term "size parameter" of a particle may be assigned the character "$\alpha$" and is defined by Mie as follows:

$$\alpha = \frac{2\pi}{\lambda_o} m_2 a \qquad (1)$$

where $m_2$ is the index of refraction of the medium in which the particle is entrained, $a$ is the radius of the particle, and $\lambda_o$ is the free space wavelength of the incident radiation on the particle.

The term "relative refractive index" is assigned the character "m" and may be defined as follows:

$$m = \frac{m_1}{m_2} \qquad (2)$$

where $m_1$ is the index of refraction of the particle.

The term "sensitivity limit of detection" of a particle is assigned the character "S" and may be defined as follows:

$$S = |(m-1)|\alpha \qquad (3)$$

It is believed advantageous to provide a particle counting apparatus adapted to count particles each having an index of refraction close to that of the medium in which it is entrained and a radius on the order of 0.05 micrometers. In terms of The Mie Theory, for incident radiation with free space wavelength on the order of 0.633 micrometers, $m_1$ on the order of 1.59 and $m_2$ on the order of 1.33, such a particle has a sensitivity limit of detection S of at least 0.129.

SUMMARY OF THE INVENTION

The instant invention relates to a radiation scattering particle counting apparatus for counting and resolving particles each having a size (i.e., radius) that is small as compared to the wavelength of incident radiation and/or has an index of refraction that is close to the medium in which it is entrained. In addition, the invention relates to a cuvette, or sample cell, configured to brightly illuminate a viewing zone through which the fluid-entrained particles pass. The invention is particularly adapted to detect and to resolve particles which have a sensitivity limit of detection S of at least 0.129, where S is defined as set forth above.

The cuvette is formed of a material transparent to focused radiation at a predetermined wavelength and exhibits an index of refraction close to the index of refraction of the medium in which the particles are entrained. The cuvette is provided with a cylindrical bore extending therethrough, the axis of the bore being parallel to the direction of particle flow through the cuvette. The cuvette is adapted to optically define and brightly illuminate a viewing zone on the interior thereof through which the particles entrained in the medium pass. The cuvette also exhibits a surface, preferably cylindrical, on the exterior thereof. The axis of the cylinder on which the surface lies is perpendicular to the axis of the bore such that the surface of the bore and the exterior surface of the cuvette are cooperable with the medium flowable therethrough to define an optical system adapted to collect light that is scattered in a relatively large solid angle from particles passing through the optically defined viewing zone disposed within the cuvette. The cuvette also exhibits, in the preferred case, an optically fine planar surface on an exterior portion thereof, the planar surface being perpendicular to the axis of the cylindrical exterior surface.

BRIEF DESCRIPTION OF THE DRAWINGS

The invention will be more fully understood from the following detailed description thereof taken in connection with the accompanying drawings which form a part of this application and in which:

FIG. 1 is a stylized pictorial representation of a particle counting system in accordance with the present invention;

FIGS. 2A and 2B are, respectively, plan and side elevational views of a cuvette adapted for use in a particle counting apparatus in accordance with the present invention;

FIG. 3 is a stylized schematic representation of the scattering and collection of radiation by particles passing through a viewing zone in a cuvette such as that shown in FIG. 2.

DETAILED DESCRIPTION OF THE INVENTION

Figure 4:
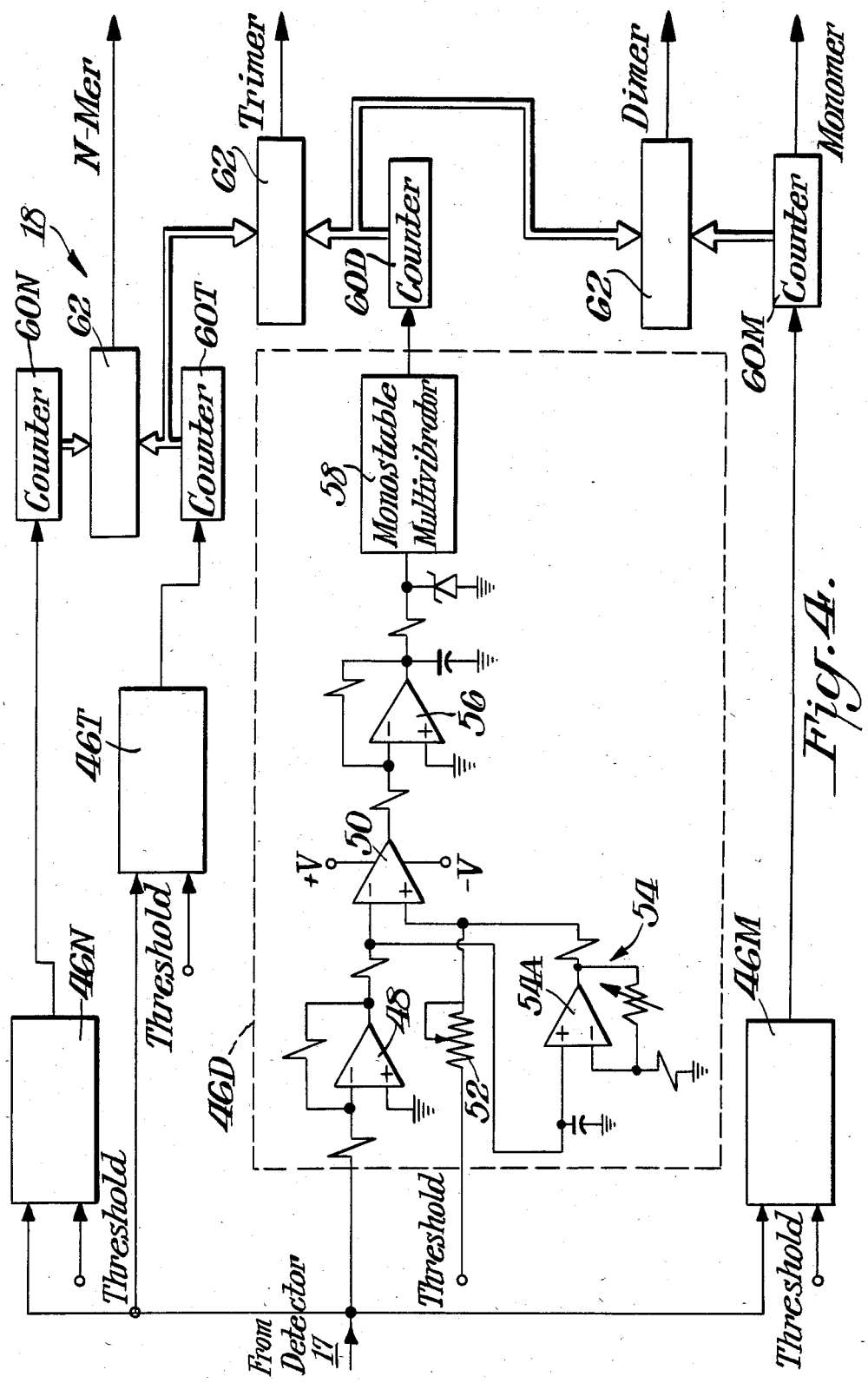
FIG. 4 is a schematic diagram of an electrical circuit adapted for use in a particle counting apparatus according to the present invention.

Throughout the following detailed description similar reference numerals refer to similar elements in all figures of the drawings.

Shown in FIG. 1 is a stylized pictorial representation of a particle counting apparatus generally indicated by reference character 10 in accordance with the present invention. The particle counting apparatus 10 includes a source 15 of collimated radiation at a predetermined wavelength (typically 0.633 micrometers), a cuvette or sample cell 16 through which flows a carrier fluid medium stream having particles to be counted entrained therein, and a detector 17 responsive to the intensity of radiation scattered by each particle in the stream to generate an electrical signal functionally related to the size thereof. A counter network 18 is operatively associated with the detector 17 to provide a count of the number of particles in the stream that fall within a predetermined size range. The cuvette 16 in accordance with this invention is disposed at the intersection of a first (incident) optical path generally indicated by reference character 22 and a second (collection) optical path generally indicated by reference character 24. The incident path 22 is preferably, but not necessarily, perpendicular to the collection path 24.

The first optical path 22 includes the radiation source 15. The source 15 produces the collimated radiation (indicated by reference character 25) which is directed toward a focusing objective lens 28. The objective lens 28 focuses the radiation, as shown by reference character 29, toward the cuvette 16. These elements, in cooperation with the geometry of the cuvette 16 to be discussed herein, serve to optically define and brightly illuminate a generally cylindrical viewing zone 30 (seen in FIG. 3) defined in the interior of the cuvette 16. In accordance with the present invention the viewing zone 30 exhibits a volume of about one picoliter (i.e., $10^{-12}$ liters). This volume corresponds to the volume of a cube 0.1 mm on a side. By keeping the volume of the viewing zone 30 as small as practicable, the radiation collected by the detector 17 from Rayleigh scattering due to the carrier fluid medium (typically water, $m_2 = 1.33$) in the viewing zone 30 is reduced. Thus, a relatively high particle density fluid stream (on the order of $10^{11}$ particles/liter) having particles each with a size (i.e., radius) that ranges as low as 0.05 micrometers, having an index of refraction on the order of 1.59 ($m_1 = 1.59$) and thus a sensitivity limit of detection S (as defined above) of at least 0.129 may be detected, resolved and counted. Moreover, the small dimensions of the viewing zone 30 reduces the probability of simultaneously detecting two particles in the viewing zone. Preferably the source 15 is a laser, such as a two milliwatt helium-neon apparatus, which provides intense diffraction-limited illumination of the viewing zone 30. Of course, any suitable source of intense diffraction-limited illumination may be utilized.

The second optical path 24 includes a positive objective lens 34 which collects radiation scattered in a cone as indicated by reference character 35. The objective lens 34 focusses and directs the collected radiation, as shown by reference character 36, toward a slit mask 37 disposed in front of the detector 17. These elements cooperate with the geometric configuration of the cuvette 16 to collect radiation scattered in the cone 35 with a relatively large (0.4) numerical aperture 40.

Referring to FIGS. 2A and 2B shown respectively are a plan and a side elevational view of a cuvette 16 in accordance with the present invention. The cuvette 16 is a substantially cylindrical member fabricated of Pyrex ® glass although any material that is transparent to the radiation emitted by the source 15 and scattered by the particles may be used. The material used to fabricate the cuvette 16 exhibits an index of refraction that is selected to be close to the index of refraction of the carrier fluid medium in which the particles are entrained so as to minimize internal reflectance of scattered light at the interface between the cuvette and the medium. The cuvette may be fabricated in any suitable manner, including injection molding.

A smooth bore 16B extends through the cuvette 16 to define a flow channel through which the carrier fluid medium carrying the particles to be counted may pass. The axis 16A of the bore 16B is parallel to the direction of fluid flow (i.e., perpendicular to the plane of FIG. 1). Preferably the axis 16A is coincident with the axis of the cuvette 16. The length of the cuvette 16 should be at least about ten times and is preferably, but not necessarily, about twenty-five times the diameter of the bore 16B.

The exterior of the cuvette 16 which is presented to the first optical path 22 is provided with a planar flattened portion 16F. This flattened portion 16F is provided with an optically smooth surface. The portion 16F extends for a distance along the height of the cuvette 16 sufficient to permit substantially aberration free illumination of the viewing zone 30 by radiation introduced thereinto from the source 15 along the first optical path 22. The exterior surface of the cuvette 16 is also provided with an indented cylindrical notch 16N. The cylindrical surface of the notch 16N has an axis 16S that is preferably oriented at a right angle to the axis 16A of the bore 16B. In the preferred case where the incident optical path 22 is perpendicular to the collection optical path 24 the axis 16S of the surface of the notch 16N also extends perpendicularly to the surface of the flattened portion 16F. Of course, this relationship is suitably modified to conform to the angle between the incident and collection paths. The radius 16R of the cylinder on which lies the surface of the cylindrical notch 16N is typically larger than the radius of the bore 16B. The dimension of the radius 16R of the indented cylindrical surface 16N is selected by geometric ray tracing techniques based upon the refractive indices of the carrier fluid medium and the material of the cuvette 16 to permit near aberration free collection of the radiation scattered from the particles passing through the viewing zone 30.

The cylindrical notch 16N compensates for the astigmatism introduced into the portion 35 of the collection optical path 24 by the differences in indices of refraction of the cuvette 16 and the carrier fluid medium and by the curvature of the bore 16B. Correction for this astigmatism is best done relatively near to the bore 16B and is necessary only in the collection optical path 24 due to the relatively large numerical aperture (i.e., 0.4) of the portion 35 of the collection path 24 as compared to the numerical aperture of the portion 29 of the incident optical path 22 (numerical aperture typically 0.02). The cylindrical notch 16N is sized so that the positive objective lens 34 may be inserted into the notch 16N and positioned close to the bore 16B. The concave surfaces of the cylindrical bore 16B and of the notch 16N form an orthogonal pair of negative cylindrical optical surfaces adapted to provide a numerical aperture of at least 0.4 to the objective 34. This large numerical aperture enables one to observe radiation scattered from a small particle over a wide range of angles to thereby enhance the detectability of such a particle.

The particle counting apparatus in accordance with the present invention is especially useful in connection with the performance of an immunoassay such as that disclosed and claimed in the above-referenced copending application of S. D. Abbott et al. titled "Particle Reagent Size Distribution Measurement for Immunoassay." The operation of the system 10 utilizing the particle counting apparatus 12 having the cuvette 16 therein for such an immunoassay is schematically shown in FIG. 3. The carrier fluid medium having a random stream of monomer, dimer, trimer or N-mer sized particles is passed through the cylindrical bore 16B and through the viewing zone 30 optically defined therein. The index of refraction of the particles is close to the index of refraction of the carrier fluid medium. It is this condition, coupled with the small size of the particles, that makes their detection for counting purposes difficult. Typically, such particles have a sensitivity limit of detection S (as defined above) of at least 0.129.

The radiation from the source 15 is focused into the viewing zone 30 by the action of the objective 28 and the surface 16F on the cuvette 16. The radiation which is scattered by particles passing through the viewing zone 30 and which appears within the light collection cone 35 is collected by the combined effects of the elements of the optical collection system including the carrier fluid medium, the bore 16B, the notch 16N and the objective 34 (not shown in the schematic illustration of FIG. 3). The cone 36 represents only the scattered light which is incident upon the detector 17 and includes the illuminated viewing zone imaged on a slit in the mask 37 perpendicular to the optical axis (also not shown in the schematic illustration of FIG. 3). Thus, the intensity of the radiation scattered by particles in the viewing zone 30 and collected by the collection optics is in proportion to the magnification of the collection optics and to the width of the slit in the mask 37. Radiation passing through the slit in the mask 37 is detected by the detector 17, typically a photodetection assembly such as that manufactured and sold by RCA under model number PF1006.

The output of the detector 17 is a series of pulses 42 the amplitude of which is related to the size of the particles from which radiation is scattered and the duration t of which (FIG. 3) is related to the residence time of the particle in the viewing zone. When used to practice the process described in the referenced copending application of S. D. Abbott et al., monomer, dimer, trimer and N-mer particles generate pulses of respectively increasing amplitude. This characteristic provides a convenient way whereby a count of particles within each respective range of sizes may be obtained.

Accordingly, the output of the detector 17 is connected to the counter network 18 which includes four separate channels: one channel (46M) for a monomer particle count; a second channel (46D) for a dimer particle count; a third channel (46T) for a trimer particle count and a fourth channel (46N) for an N-mer particle count. The detailed schematic diagram of a suitable counter network 18 is shown in FIG. 4. In FIG. 4 the dimer count channel 46D, which is a typical one of the channels 46, is illustrated in more detail.

The output of the detector 17 is amplified by an amplifier 48, such as a device manufactured by Texas Instruments and sold under model number TL080. The output of the amplifier 48 is applied to the inverting input of an FET operational amplifier 50 such as that manufactured by Burr-Brown and sold under model number 3550 configured as a differential amplifier. The threshold of the differential amplifier 50 is made variable to define a predetermined threshold for each channel under consideration by the inclusion of a potentiometer 52 connected to the noninverting input to the amplifier 50. The threshold is continuously adjusted to accommodate fluctuations in the detector output by the action of a compensating network 54 that includes an operational amplifier 54A, such as that sold by National Semiconductor under model number 741.

When the signal applied to the inverting terminal of the amplifier 50 exceeds the adjusted threshold level applied at its noninverting terminal, an output signal is generated and applied (after appropriate inversion and amplification by an amplifier 56) to a monostable multivibrator 58 such as that sold by Fairchild under model number 74121. The amplifier 56 is similar to the amplifier 48. The output of the device 58 is connected to a digital counter 60D such as that manufactured by Princeton Applied Research, Inc. under model number 1109.

Each channel 46 operates in an analagous manner to produce an output which increments an associated counter 60. However, due to the relationship of the signals produced by the detector 17, a pulse 42 produced by an N-mer particle will exceed the thresholds for each channel 46M, 46D, 46T and 46N and will simultaneously increment the respective counters 60 associated with each of those channels. The magnitude of a pulse produced by a trimer particle will increment the counters associated with the channels 46M, 46D and 46T. Similarly, a dimer particle results in the incrementing of the counters associated with channels 46M and 46D. A monomer particle increments only the counter associated with the channel 46M. Accordingly, to obtain a count of each particle in each size range, an array of arithmetic logic units 62 or other suitable functional elements is connected to provide signals indicative of the number of N-mers (the difference between the counters 60N and 60T), the number of trimers (the difference between the counters 60T and 60D) and the number of dimers (the difference between the counters 60D and 60M). The number of monomer particles is obtained directly from the counter 60M.

Of course, any alternative counting arrangement may be utilized and remain within the contemplation of the present invention. For example a suitably interfaced and programmed microcomputer controlled arrangement may be used to accomplish this task. Using a single comparator such as the comparator 50, the output of which is connected to a frequency-to-voltage converter and the noninverting input of which receives a programmable input threshold (both being read or varied, respectively, by the microcomputer) one could sweep through values of threshold and record resulting voltages to obtain a "greater than" plot of pulse heights for the sample. A frequency-to-voltage converter such as sold by Dynamic Measurements Corp. under model 9110 and a Digital Equipment Corp. MINC computer can be utilized.

From the foregoing it may be appreciated that a particle counting apparatus has been disclosed which is able to detect, resolve and count particles having a sensitivity limit of detection S, as defined above, of at least 0.129. Those skilled in the art, having the benefit of the teachings of the present invention as hereinabove set forth may effect numerous modifications thereto. These modifications are to be construed as lying within the scope of the present invention, as set forth in the appended claims.

What is claimed is:

1. A cuvette for use in a radiation scattering particle counting apparatus adapted to count particles entrained in a medium flowable through the cuvette, the cuvette being adapted to optically define and brightly illuminate a viewing zone on the interior thereof through which the particles entrained in the medium pass, the particles each having a radius that is small as compared to the wavelength of the incident radiation and an index of refraction that is close to the index of refraction of the medium such that the particles each have a sensitivity limit of detection S of at least 0.129, the cuvette being formed from a material transparent to focused radiation and exhibiting an index of refraction close to the index of refraction of the medium, the cuvette having a cylindrical bore extending therethrough the axis which is parallel to the direction of particle flow through the cuvette, the cuvette also having a cylindrical surface on the exterior thereof, the axis of the cylinder on which the surface lies being perpendicular to the axis of the bore.

2. The apparatus of claim 1 wherein the radius of the exterior cylindrical surface is greater than the radius of the bore.

3. The apparatus of claim 2 further comprising an optically fine planar surface on the exterior of the cuvette.

4. The apparatus of claim 3 wherein the planar surface extends perpendicular to the axis of the exterior cylindrical surface.

5. The apparatus of claim 4 wherein the exterior cylindrical surface is sized to receive a positive objective lens, the surface of the cylindrical bore and the exterior cylindrical surface being cooperable to define an orthogonal pair of negative cylindrical optical surfaces to provide a numerical aperture of at least 0.4 to the objective lens.

6. The apparatus of claim 3 wherein the exterior cylindrical surface is sized to received a positive objective lens, the surface of the cylindrical bore and the exterior cylindrical surface being cooperable to define an orthogonal pair of negative cylindrical optical surfaces to provide a numerical aperture of at least 0.4 to the objective lens.

7. The apparatus of claim 1 further comprising an optically fine planar surface on the exterior of the cuvette.

8. The apparatus of claim 7 wherein the planar surface extends substantially perpendicularly to the axis of the exterior cylindrical surface.

9. The apparatus of claim 8 wherein the exterior cylindrical surface is sized to receive a positive objective lens, the surface of the cylindrical bore and the exterior cylindrical surface being cooperable to define an orthogonal pair of negative cylindrical optical surfaces to provide a numerical aperture of at least 0.4 to the objective lens.

10. The apparatus of claim 7 wherein the exterior cylindrical surface is sized to receive a positive objective lens, the surface of the cylindrical bore and the exterior cylindrical surface being cooperable to define an orthogonal pair of negative cylindrical optical surfaces to provide a numerical aperture of at least 0.4 to the objective lens.

11. A radiation scattering particle counting apparatus for counting particles entrained in a fluid medium, the particles each having a radius that is small as compared to the wavelength of the incident radiation and an index of refraction that is close to the index of refraction of the medium such that the particles each have a sensitivity limit of detection S of at least 0.129, the apparatus comprising:

a source of focused radiation;

a cuvette formed of a material transparent to the radiation and having an index of refraction close to the index of refraction of the medium, the cuvette having a cylindrical bore formed therein through which a fluid medium having particles entrained therein is flowable, the cuvette also having a cylindrical surface formed on the exterior thereof with the axis of the exterior surface being perpendicular to the axis of the bore, the cuvette being adapted to optically define and brightly illuminate a viewing zone on the interior thereof through which the particles entrained in the medium pass; and, a detector responsive to radiation scattered by a particle passing through the viewing zone defined within the cuvette to generate an electrical signal functionally related to the size of the particle.

12. The apparatus of claim 11 wherein the radius of the exterior cylindrical surface is greater than the radius of the bore.

13. The apparatus of claim 12 wherein the cuvette further comprises an optically fine planar surface on the exterior thereof.

14. The apparatus of claim 13 wherein the planar surface extends perpendicular to the axis of the exterior cylindrical surface.

15. The apparatus of claim 14 wherein the exterior cylindrical surface is sized to receive a positive objective lens, the surface of the cylindrical bore and the exterior cylindrical surface being cooperable to define an orthogonal pair of negative cylindrical optical surfaces to provide a numerical aperture of at least 0.4 to the objective lens.

16. The apparatus of claim 13 wherein the exterior cylindrical surface is sized to receive a positive objective lens, the surface of the cylindrical bore and the exterior cylindrical surface being cooperable to define an orthogonal pair of negative cylindrical optical surfaces to provide a numerical aperture of at least 0.4 to the objective lens.

17. The apparatus of claim 11 wherein the cuvette further comprises an optically fine planar surface which on the exterior thereof.

18. The apparatus of claim 17 wherein the planar surface extends substantially perpendicularly to the axis of the exterior cylindrical surface.

19. The apparatus of claim 18 wherein the exterior cylindrical surface is sized to receive a positive objective lens, the surface of the cylindrical bore and the exterior cylindrical surface being cooperable to define an orthogonal pair of negative cylindrical optical surfaces to provide a numerical aperture of at least 0.4 to the objective lens.

20. The apparatus of claim 17 wherein the exterior cylindrical surface is sized to receive a positive objective lens, the surface of the cylindrical bore and the exterior cylindrical surface being cooperable to define an orthogonal pair of negative cylindrical optical surfaces to provide a numerical aperture of at least 0.4 to the objective lens.

* * * * *